United States Patent [19] [11] Patent Number: 5,262,330
Chapoteau et al. [45] Date of Patent: Nov. 16, 1993

[54] COLORIMETRIC METHODS AND REAGENTS FOR THE ASSAY OF CALCIUM IN A TEST SAMPLE

[75] Inventors: Eddy Chapoteau, Brooklyn; Bronislaw P. Czech, Peekskill; Wolodymyr I. Zazulak, East Elmhurst, all of N.Y.

[73] Assignee: Miles Inc., Tarrytown, N.Y.

[21] Appl. No.: 842,860

[22] Filed: Feb. 27, 1992

[51] Int. Cl.$^5$ .................. G01N 33/84; G01N 33/20; C09B 29/00

[52] U.S. Cl. ............................ 436/79; 422/57; 422/56; 436/74; 436/164; 436/169; 534/689; 534/691; 534/764; 534/770; 534/821; 534/829; 534/853

[58] Field of Search .................... 422/56-58; 436/74, 79, 164, 169; 534/689, 691, 764, 770, 821, 829, 853; 546/264, 329; 562/426, 430, 441, 452, 457

[56] References Cited

U.S. PATENT DOCUMENTS

| | | | |
|---|---|---|---|
| 2,010,512 | 8/1935 | Ebert | 534/829 X |
| 2,583,890 | 1/1952 | Schwarzenbach | 436/79 X |
| 2,709,178 | 5/1955 | Schläpfer et al. | 436/79 X |
| 2,745,720 | 5/1956 | Schwarzenbach et al. | 436/79 X |
| 3,301,870 | 1/1967 | Terzijska et al. | 436/79 X |
| 3,509,122 | 4/1970 | Horstmann et al. | 534/691 X |
| 3,549,358 | 12/1970 | Clecak et al. | 534/689 X |
| 3,754,865 | 8/1973 | Gindler | 436/74 X |
| 4,382,122 | 5/1983 | Mezei et al. | 436/74 |
| 4,446,321 | 5/1984 | Schmidt et al. | 546/94 X |
| 4,603,209 | 7/1986 | Tsien et al. | 548/236 |
| 4,795,712 | 1/1989 | Toner et al. | 436/79 |
| 4,848,362 | 7/1989 | DeMarinis et al. | 436/79 |
| 4,859,606 | 8/1989 | Cram et al. | 436/79 |
| 4,992,381 | 2/1991 | Cram et al. | 436/79 X |

FOREIGN PATENT DOCUMENTS

0335136  10/1989  European Pat. Off. ............ 436/79

OTHER PUBLICATIONS

Rees et al., *J. Chem. Soc.*, 1961, 5101–5105.
H. Flaschka et al., "Metal Indicators. VII. A Ohthalein responding to Alkaline Earth Ions and its Analytical Application", *Helvetica Chimica Acta*, 1954, 37, 113–120.
*Biochem.*, vol. 19, (1980), "New Calcium Indicators and Buffers with . . . Prototype Structures", Roger Y. Tsien, pp. 2396–2404.
*Journal of Biological Chemistry*, vol. 260, (1985), "New Generation . . . ", G. Grynkiewicz et al., pp. 3440–3450.
*J. Am. Chem. Soc.*, vol. 111, (1989), "Biologically Useful Chelators That Take Up Ca$^{2+}$ upon Illumination", S. R. Adams et al., pp. 7957–7968.

*Primary Examiner*—James C. Housel
*Assistant Examiner*—Arlen Soderquist
*Attorney, Agent, or Firm*—Andrew L. Klawitter

[57] ABSTRACT

A chromogenic compound found to be especially selective in the determination of calcium in blood of the general formula (I):

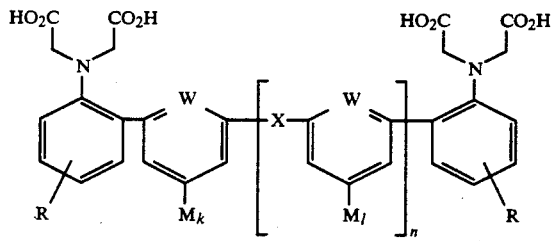

where:
R is hydrogen or lower alkyl;
X is $CH_2$, $CH_2CH_2$, CH=CH, O, S, $SO_2$, S—S, or NR;
X is CH, C—OH or N;
M is p-nitrophenylazo, 2,4-dinitrophenylazo, 2,4,6-trinitrophenylazo, p-nitrostyryl, p-benzoquinoneimino, bis-(4-dimethylaminophenyl) hydroxymethyl, 3-phenylisothiazolyl-5-azo, thiazolyl-5-azo, or isothiazolyl-5-azo;
k is 1;
l is 0 or 1; and
n is 0 or 1.

12 Claims, 6 Drawing Sheets

COLORIMETRIC METHODS AND REAGENTS FOR THE ASSAY OF CALCIUM IN A TEST SAMPLE

BACKGROUND OF THE INVENTION

1. Field of the Invention

The present invention relates to a novel methods and reagents useful for the measurement of calcium ions, in Particular, calcium ions in blood and other physiological fluids. 2 Description of the Prior Art Calcium is an important electrolyte whose monitoring aids the physician in evaluation of patient's health. Changes in calcium level which usually is relatively stable in most body fluids (in blood from 8.2 to 10.3 mg/dl) may indicate presence of various pathological conditions. Calcium levels significantly lower than normal may indicate hypoparathyroidism, vitamin D deficiency or nephritis. Values greater than normal may indicate hyperparathyroidism, vitamin D intoxication or myeloma. Thus, to detect any disease early, which would be manifested by an abnormal calcium level, the method for calcium measurement has to be very accurate and precise.

A number of chemical and physical procedures are known for the determination of calcium. Direct colorimetric procedures are preferred over tedious precipitation, gravimetric or titrimetric procedures. Generally, such colorimetric procedures involve the complexation of a dye with calcium ions to provide a measurable shift in dye absorption.

A potential problem in the determination of calcium ions in most fluids is the presence of potentially interfering ions (for example, magnesium or iron) or large molecules (for example, proteins or bilirubin). Magnesium ions present a particularly difficult problem because they tend to complex to the same compounds that complex with calcium ions. Accordingly, the prior art has developed procedures whereby magnesium ions can be removed physically from the test sample prior to calcium determination or masked with a magnesium-specific complexing reagent.

Highly selective compounds for calcium ions are described by Tsien in *Biochem.*, 19, pp. 2396-2404 (1980). The parent compound described therein is 1,2-bis(o-aminophenoxy)ethane-N,N,N',N'-tetraacetic acid, commonly known as BAPTA. These compounds absorb in the ultraviolet region of the electromagnetic spectrum. This is a significant disadvantage as other species, such as bilirubin, hemoglobin and other porphorin species and metabolic by-products of porphyrins, found in analyte solutions such as blood plasma, spinal fluid, urine and other body fluids, also absorb in the UV and short visible wavelength portions of the electromagnetic spectrum, and produce background interference with standard colorimetric equipment and procedures. Therefore, it was thought desirable to have highly selective calcium complexing compounds which would be detectable at longer wavelengths, and which would shift to other wavelengths when complexed with calcium to allow quantitative analysis for calcium without interference from UV and short wavelength visible light-absorbing species. U.S. Pat. No. 4,795,712 to Toner, et al. describes such calcium complexing dyes. Chromogenic derivatives of 1,2-bis(o-aminoaryloxy)ethane-N,N,N',N'-tetraacetic acid are useful for the determination of calcium ions in both solution and dry assays are disclosed. These compounds comprise a dye moiety which is directly conjugated to the acetic acid substituted-nitrogen atom, and which enables the compounds to exhibit maximum absorbance at a wavelength generally greater than 400 nm before complexation. When the compounds are complexed with calcium ions, the absorbance shifts to a shorter wavelength.

Fluorescent intracellular calcium indicators based on tetracarboxylic compounds are reported in U.S. Pat. No. 4,849,362. The compounds have longer absorption wavelength characteristics which make them useful for multiparameter flow cytometric analysis of intracellular calcium ion concentrations in mixed cell populations.

The orthocresolphthalein complexone method (CPC method), based on a tetracarboxylic acid chelate, first described by A. G. Flaschka, et al., Helv. Chim. Acta 1954, 37, 113, is considered to be the most acceptable calcium method by clinical laboratories. Despite its widespread use, the method suffers from relatively short reagent stability, sensitivity to carbon dioxide and stoichiometry dependent low end non-linearity. Moreover, this method reduces sample throughput (rate of analysis or tests per hour) on automated clinical analyzers. The chromogenic ionophores of the present invention permit the development of a single reagent method with extended stability of the reagent and full range linearity.

A major factor which has to be taken into consideration during the design of possible synthetic candidates for novel calcium chromoionophores is a bathochromic shift of the wavelength maximum upon complexation with calcium. A great number of compounds reported in the literature are derived from 1,2-bis(o-aminophenoxy)ethane-N,N',N'-tetraacetic acid, commonly known a BAPTA. The chromogenic analogs of these structures contain chromophores positioned para to the sensing nitrogen atom, and exhibit a hypsochromic shift of the wavelength maximum upon calcium binding. This in itself is an undesirable characteristic due to the potential spectral interferences present at the shorter wavelengths. In addition, the starting absorbance of the reagent is usually very high.

The CPC method employs a tetracarboxylic acid compound which incorporates two phenol subunits and a chromophore attached oara to the phenolic hydroxyls. Such configuration of the chelating sites and the chromophore system guarantees the bathochromic shift upon complexation with calcium since the cation stabilizes the excited state of the ligand. Thus, in developing new compounds, it would be advantageous to preserve a similar chromophore arrangement, but incorporate into the structure the relatively rigid tetra and triaryl backbones. The tetra and triaryl subunits have successfully been used before in the construction of sodium and potassium selective binders, and promise high degree of preorganization of the chelating sites with respect to the phenolic sensing atoms, forming a polar "nest" complementary with the calcium ion. Novel structures employing carboxylic acid moieties as the chelating groups were chosen.

The compounds of the present invention can generally be described as chromogenic octadentate tetracarboxylic-diphenol and phenol compounds that produce color change in the visible range upon interaction with calcium ions. The chromoionophore is structurally different from other known calcium complexing compounds. It incorporates four (4) acetic acid chelating groups, and one (1) or two (2) nitrophenylazophenyl chromophores attached to a rigid tetraaryl or triaryl framework. The chromogenic compound reacts with calcium ions producing a bathochromic shift and an increase in absorbance at 550 nm in proportion to calcium concentrations.

Accordingly, it has been found that the chromogenic compounds of the present invention demonstrate sensitivity to calcium ions. The chromogenic compounds can be incorporated into a single liquid reagent adapted for use on automated clinical analyzers to determine the calcium concentration in physiological fluid samples such as blood.

OBJECTS OF THE INVENTION

It is an object of this invention to provide a novel assay method and reagent composition useful for the measurement of calcium ions, in particular, calcium ions in blood and other physiological fluids.

Another object of this invention is to provide an assay method and reagent composition as above, which enable fast assay of the ion.

Yet another object of this invention is to provide an assay method and reagent composition as above which have a high degree of selectivity.

Still another object of this invention is to provide an assay method and reagent composition as above which are particularly adapted for photometric clinical analyzers.

A yet further object of this invention is to provide an assay method and reagent composition as above which provide an accurate, precise and convenient alternative to conventional methodologies.

A yet further object of this invention is to provide a dry test device in which the reagent composition, as above, is incorporated into a matrix.

A further object of this invention is to provide an assay method and reagent composition as above which permit the quantitative determination of calcium in blood serum and other biological fluids by spectrophotometric methods in a homogeneous, single phase solvent system that require no sample pretreatment.

Other objects and features of the invention will be in part apparent and in part pointed out hereinafter.

SUMMARY OF THE INVENTION

Briefly stated, the present invention resides in the discovery of a new chromogenic compound of the general formula (I):

where:
R is hydrogen, lower alkyl or lower alkenyl;
X is $CH_2$, $CH_2CH_2$, $CH=CH$; O, S, $SO_2$, S—S, NR;
W is CH, C—OH or N;
M is p-nitrophenylazo, 2,4-dinitrophenylazo, 2,4,6-trinitrophenylazo, p-nitrostyryl, p-benzoquinoneimino, bis-(4-dimethylaminophenyl) hydroxymethyl, -phenylisothiazolyl-5-azo, thiazolyl-5-azo; or isothiazolyl-5-azo;
k is 0 or 1;
l is 0 or 1; and
n is 0 or 1.

A preferred chromogenic compound of the present invention found to be especially useful in the determination of calcium in blood is a chromogenic dilabeled tetraacid diphenol based on formula (I) wherein: R is hydrogen; X is $CH_2$; W is COH; M is p-nitrophenylazo; and k, l and n are all 1. This chromoionophore has a relatively rigid tetraaryl framework with two chromophores attached thereto, and is identified chemically as bis[2-hydroxy-3-(2-aminophenyl)-5-(4-nitrophenylazo)]methane N,N,N',N'-tetraacetic acid.

The compounds of formula (I) may be incorporated into a reagent for detecting the presence of calcium in solution. Such a reagent composition comprises a compound of general formula (I), a percentage (by weight to volume) of a magnesium masking agent and a buffer. A preferred reagent composition includes the above-described preferred chromogenic dilabeled tetraacid diphenol, a volume percentage of magnesium mask of about 0.05%, and a buffer present in an amount to adjust the reagent composition pH from about 8.5 to about 9.2. A surfactant may be added to the reagent composition to increase sensitivity to calcium. An antioxidant may also be included, if desired.

Further aspects of the present invention are processes of synthesizing various chromogenic compounds of the present invention.

The scope of the invention, including the compounds, reagent compositions and their use, synthesis and preparation, and experimental results are set forth hereinbelow.

BRIEF DESCRIPTION OF THE DRAWINGS

The above and other objects and significant advantages of the present invention are believed made clear by the following detailed description thereof taken in conjunction with the accompanying drawings wherein.

DESCRIPTION OF THE PREFERRED EMBODIMENTS

The following definitions are provided to clarify the scope of the present invention, and to enable its formulation and use.

As used herein, "chromogenic" is meant that characteristic of a chemical system whereby a detectable response is generated in response to an external stimulus. Thus, for example, an ionophore is chromogenic when it is capable of exhibiting a detectable response upon complexing with an ion, which detectable response is not limited solely to change in color as defined below.

By the term "detectable response" is meant a change in or appearance of a property in a system which is capable of being perceived, either by direct observation or instrumentally, and which is a function of the presence of a specific ion in an aqueous test sample. Some examples of detectable responses are the change in or appearance of color, fluorescence, phosphorescence, reflectance, chemiluminescence, or infrared spectrum which are referred to generally as chromogenic responses. Other examples of detectable responses may be the change in electrochemical properties, PH and nuclear magnetic resonance.

The term "lower alkyl" as used in the present disclosure, includes an alkyl moiety, substituted or unsubstituted, containing about 1-4 carbon atoms. Included in the meaning of lower alkyl are methyl, ethyl, n-propyl, isopropyl, n-butyl, sec-butyl and tert-butyl. These may be unsubstituted, or they may be substituted provided any such substituents do not interfere with the operation or functioning of the presently claimed test means or device in its capability to detect calcium ions. "Aryl" as used herein includes substituted or unsubstituted aryl moieties containing 6-12 carbon atoms, such as for example, phenyl, tolyl, butyl phenyl, naphthyl ethyl, chlorophenyl, nitrophenyl and carboxyphenyl. "Lower alkenyl" means vinyl or lower alkyl substituted vinyl.

The compound of formula (I) includes as part of its structure a particular kind of chemically configured moiety which is capable of changing its physico-chemical characteristics when a complex is formed by the calcium ion and compound of general formula (I). That is to say, if the calcium ion is present in a test sample whether or not other ions are present, a detectable change in those physico-chemical properties takes place. This capability to exhibit such a response to complexation contributes greatly to the usefulness of compound (I) in assaying the analyte or target ion.

The compounds of formula (I) previously described can be incorporated in a reagent composition which, when prepared as an aqueous solution, was found useful for detecting the presence of calcium ions. Since the compounds of formula (I) show a tendency to complex with magnesium ions as well as calcium ions, a masking agent is needed to eliminate spectral interference from the magnesium ions which are present in human serum and other biological fluids. A preferred reagent composition includes, in addition to the preferred chromogenic dilabeled tetraacid-diphenol, a magnesium mask at a concentration of 0.05% (weight to volume). Examples of a suitable masking agents are 8-hydroxyquinoline and 8-hydroxyquinoline-5-sulfonic acid. Other suitable masking agents useable in the present invention would readily come to mind to those skilled in the art.

The reagent composition also includes a buffer to provide a pH environment of from about 8.5 to about 9.2.

It has been found that the addition of a surfactant to the reagent increases the spectral response of the chromoionophore to calcium thereby permitting more accurate, precise analysis of calcium in the sample. A surfactant such as a polyethylene oxide alkyl ether, for example, surfactants sold under the trade designation Brij 35, Tergitol TMN6 and Triton X-100 may be employed.

An anti-oxidant may be included as well in the reagent. In addition, the reagent composition may contain manufacturing excipients, stabilizers and other inert ingredients, all of which are easily within the knowledge of one skilled in the art, or which could be routinely determined without the need for undu experimentation.

The reagent composition may be in liquid form when used, or may be impregnated into a suitable carrier matrix to form a test device. The device can take on such formats as a dip-and-read strip for urine or a test slide for use with an automatic blood analyzer, or can form a multi-layer structure such as is described in U.S. Pat. Nos. 3,992,158 and 4,292,272.

EXPERIMENTALS

The following examples set forth various aspects of the subject invention. It will be understood that the formulations and procedures which follow are provided for the purpose of illustration only, and that other ingredients, proportions and procedures can be employed in accordance with the disclosures of this invention.

Materials and Methods

Unless specified otherwise, reagent grade reactants and solvents were used as received from chemical suppliers. Toluene and acetonitrile were dried over molecular sieves (4-A). Acetone was dried over anhydrous potassium carbonate. Radical free tetrahydrofuran (THF) was distilled from sodium benzophenone ketyl prior to use.

Melting points were determined on a Thomas-Hoover capillary apparatus. $^1$H NMR spectra were measured with a Varian Gemini 200 MHz spectrometer and chemical shifts are reported in parts per million ($\delta$) downfield from tetramethylsilane. Elemental analysis was performed by SPANG Microanalytical Laboratory of Eagle Harbor, Mich.

I. Synthesis of Chromogenic Dilabeled Tetraacid-diphenol (9)

Figure 1:
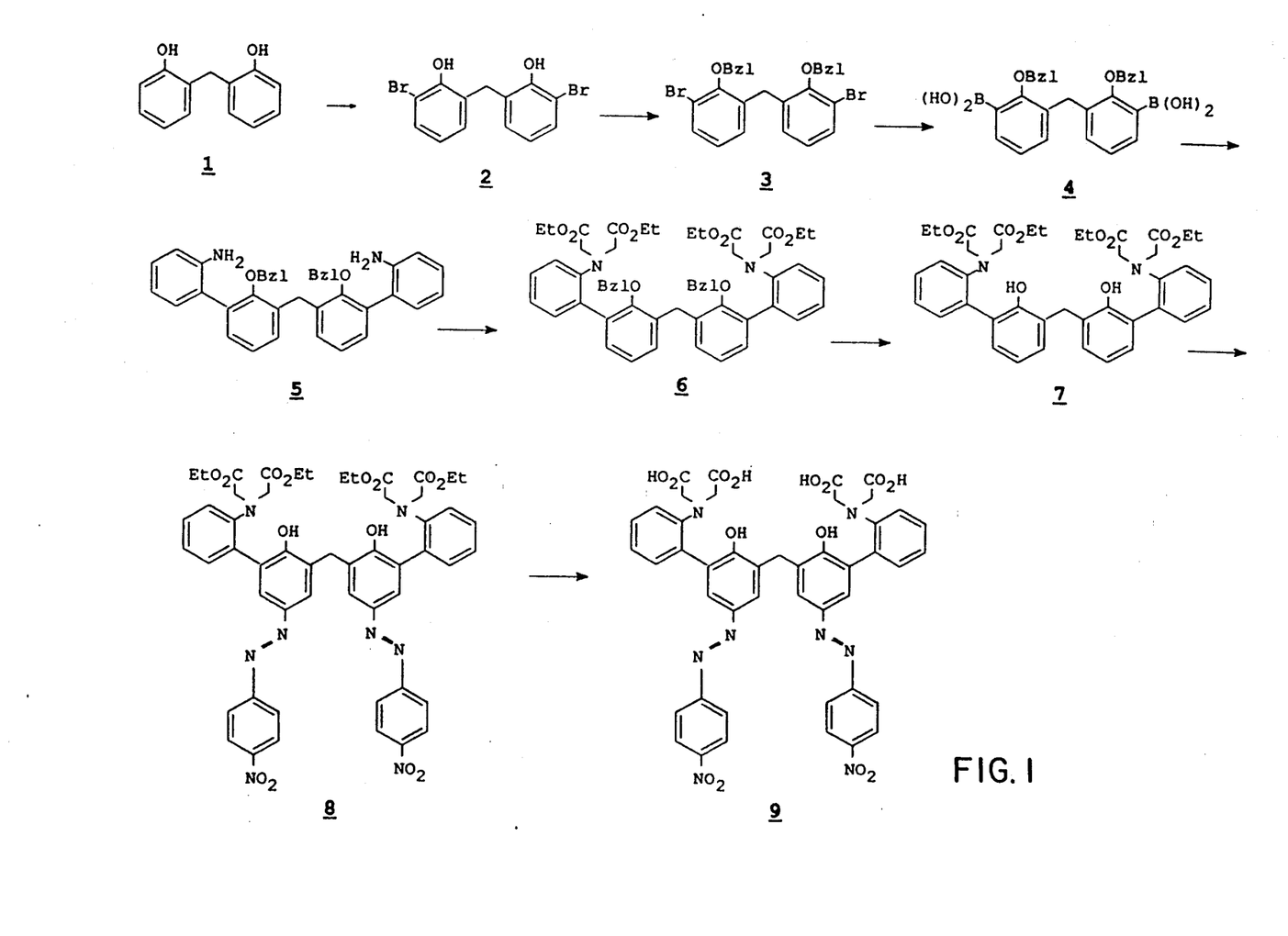
FIG. 1 describes a reaction pathway for synthesizing a chromogenic dilabeled tetraacid-diphenol of the present invention.

The synthesis sequence is illustrated in FIG. 1, and is described below.

Preparation of Compound (2)

Bromine (16.0 g, 100 mmol) was added dropwise to a solution of t-butylamine (14.6 g, 200 mmol) in dry toluene (250 ml) at $-30°$ C. The solution was cooled to $-75°$ C., and a solution of bisphenol (1) (10.0 g, 49.9 mmol) in CH (150 ml) was added and the reaction mixture was allowed to warm up to room temperature overnight. Water (50 ml) was added, and after stirring vigorously for 20 min., the organic layer was separated and washed with 15% NaOH (2×30 ml). The combined aqueous extracts were cooled to $-20°$ C. acidified with 6N HCl to pH of approximately 2 and extracted with $CH_2Cl_2$ (2×30 ml). The organic extracts were dried ($MgSO_4$), the solvent was removed in vacuo and the residue was purified on a silica gel column with petroleum ether/$CH_2Cl_2$ (1:1) as eluent to give dibromide (2) (12.8 g, 72%) as a white solid with mp 92°-93.5° C.; $^1$H NMR ($CDCl_3$): $\delta$ 4.02 (s, $CH_2$, 2H), 5.75 (br s, OH, 2H), 6.73 (t, ArH, 2H), 7.09 (d, ArH, 2H), 7.33 (d, ArH, 2H); Anal. Calcd. for $C_{13}H_{10}Br_2O_2$: C, 43.61; H, 2.82. Found: C, 3.63; H, 2.73.

Preparation of Compound (3)

A mixture of dibromide (2) (15.2 g, 42.4 mmol), benzyl bromide (24.25 g, 141.6 mmol) and anhydrous K (21.3 g, 154 mmol) in dry acetone was stirred and refluxed under argon for 48 h. The solvent and the excess benzyl bromide were distilled off under reduced pressure. The residue was partitioned between $CH_2Cl_2$ and water. The organic layer was dried ($MgSO_4$) and the crude product was chromatographed on a silica gel column with $CH_2Cl_2$-petroleum ether (1:1–3:1) as eluent to afford (3) (22.8 g, 100%) as a colorless viscous oil; $^1H$ NMR ($CDCl_3$): δ 4.02 (s, $ArCH_2Ar$, 2H), 4.82 (s, $ArCH_2O$, 4H), 6.75–7.02 (m, ArH, 4H), 7.28–7.52 (m, ArH, 12H); Anal. Calcd. for $C_{27}H_{22}Br_2O_2$: C, 60.25; H, 4.12. Found: C, 60.36; H, 4.21.

Preparation of Compound (4)

n-Butyllithium (2.4 M) (22 ml, 52 mmol) was added at −78° C. to a solution of compound (3) (11.5 g, 22.1 mmol) in dry THF (300 ml). After 10 min. the solution was cannulated into a solution of trimethylborate (63.4 g, 610 mmol) in THF (80 ml), also cooled to −78° C. The resultant mixture was stirred at −78° C. for 30 min., allowed to warm up to 0° C. over 1 h, and 2N HCl (160 ml) was added. After stirring for 1h, ether (150 ml) was added and the stirring was continued for another 4 h. The organic layer was separated, and the aqueous layer was extracted with ether (3×50 ml). The combined ether layers were extracted with 3N NaOH (3×100 ml), the aqueous extracts were combined and acidified with concentrated HCl at 0° C. A white solid suspension was kept overnight in a refrigerator at 4° C., filtered, washed with water, and dried under vacuum to produce boronic acid (4) (6.4 g, 62%) as a white solid; $^1H$ NMR ($CD_3OD$): δ 4.00 (s, $ArCH_2Ar$, 2H), 4.70 (s, $ArCH_2O$, 4H), 6.95–7.50 (m, ArH, 16H).

Preparation of Compound (5)

A mixture of o-iodoaniline (5.00 g, 22.8 g), boronic acid (4) (4.86 g, 10.4 mmol), tetrakis(triphenylphosphine)palladium (0.34 g, 0.30 mmol), 2M aqueous Na (30 ml), EtOH (16 ml), and benzene (60 ml) was heated at 85° C. under argon for 48 h. An additional 50 mg of the catalyst was added after 24 h. The organic layer was separated, and the aqueous layer was extracted with $CH_2Cl_2$. The combined organic extracts were dried ($MgSO_4$), the solvent was removed in vacuo. and the residue was chromatographed on silica gel with petroleum ether-EtOAc (5:1) as eluent to given diamine (5) (4.48 g, 77%) as a pale-yellow glass; $^1H$ NMR ($CDCl_3$): δ 3.78 (br s, $NH_2$ 4H), 4.17 (s, $ArCH_2Ar$, 2H), 4.39 (s, $ArCH_2O$, 4H) 6.70–7.00 (m, ArH, 8H), 7.05–7.37 (m ArH, 16H). Anal. Calcd. for $C_{39}H_{34}N_2O_2$: C, 83.25, H, 6.09. Found: C, 83.24; H, 6.21.

Preparation of Compound (6)

A solution of diamine (5) (9.05 g, 16.1 mmol), ethyl bromoacetate (26.9 g, 161 mmol), and lutidine (17.2 g, 18.7 mmol) in dry $CH_3CN$ was refluxed for two days. An additional ml of ethyl bromoacetate was added, and the heating was continued for one more day. The solvent was removed in vacuo. and the residue was partitioned between $CH_2Cl_2$ and water. The organic layer was separated and the aqueous layer was extracted with $CH_2Cl_2$, the combined organic layers were dried ($Na_2SO_4$), the solvent was removed in vacuo, and the residue was chromatographed on silica gel with $CH_2Cl_2$-EtOAc (98:2–95:5) as eluent to afford tetraester (6) (7.10 g, 49%) as a pale-yellow glass; $^1H$ NMR ($CDCl_3$): δ 1.10 (t, $CH_3$, 12H), 3.60–4.45 (m, $CH_2N+CH_2O+ArCH_2Ar$, 22H), 6.85–7.60 (m, ArH, 24H); Anal. Calcd. for $C_{55}H_{58}N_2O_{10}$: C, 72.83; H, 6.44. Found: C, 72.72; H, 6.49.

Preparation of Compound (7)

A mixture of tetraester (6) (4.95 g, 5.46 mmol), 10% Pd/C (0.52 g), acetic acid (1 ml) and EtOH (125 ml) was shaken under hydrogen at 50 psi pressure over 18 h. The catalyst was removed by filtration through Celite, and the solvent was evaporated in vacuo to give compound (7) (4.0 g, 100%) as a pale-yellow glass. An analytical sample of (7) was obtained by chromatography on silica gel with $CH_2Cl_2$-EtOAc (97:3) as eluent; $^1H$ NMR ($CDCl_3$): δ 1.15 (t, $CH_3$, 12H), 3.40–4.30 m, $CH_2O+CH_2N+ArCH_2Ar$, 18H), 6.87 (t, ArH, 2H), 7.02–7.33 (m, ArH, 12H), 7.99 (s, OH, 2H); Anal. Calcd. for $C_{41}C_{46}N_2O_{10}$: C, 67.75; H, 6.38. Found: C, 67.84; H, 6.55.

Preparation of Compound (8)

A mixture of tetraester (7) (0.94 g, 1.29 mmol) in THF-$H_2O$ (1:1, 20 ml) and $NaHCO_3$ (2.6 g) was cooled to 0–5° C. and a suspension of p-nitrobenzenediazonium tetrafluoroborate (2.00 g, 8.44 mmol) in cold THF-$H_2O$ (1:1, 32 ml) was added dropwise during 40 min. The mixture, which turned from colorless to red-brown, was stirred at room temperature for 2 h. The solvent was removed in vacuo and the residue was partitioned between $CH_2Cl_2$ and water. The aqueous layer was extracted two more times with $CH_2Cl_2$, and the combined organic layers were washed with 2N HCl and dried ($Na_2SO_4$). The solvent was removed in vacuo and the residue was purified by chromatography on silica gel with $CH_2Cl_2$-EtOAc (98:2) to afford compound (8) (0.53 g, 40%) as a dark orange glass; $^1H$ NMR ($CDCl_3$): δ 1.14 (t, $CH_3$, 12H), 3.70–4.25 (m, $CH_2N+CH_2O$, 16H), 4.37 (s, $ArCH_2Ar$, 2H), 7.13–7.48 (m, ArH+OH, 9H) 7.83 (s, ArH, 4H), 8.10 (ABq, ArH, 8H), 8.92 (s, OH, 1H); Anal. Calcd. for C, 62.10; H, 5.11. Found: C, 62.27; H, 5.12.

Preparation of Compound (9)

Water (4 ml) was added to a solution of tetraester (8) (0.50 g, 0.49 mmol) in dioxane (19 ml). The mixture was cooled in an ice bath and LiOH (0.30 g, 12.5 mmol) was added. The mixture, which immediately turned violet, was stirred overnight at room temperature. The solvent was removed in vacuo and the residue was partitioned between ether and diluted HCl (pH of approximately 4). The ether layer was separated and the solvent was removed in vacuo to produce tetraacid 9 (0.48 g, about 100%) as a brown-red foam; $^1H$ NMR ($CD_3OD$): δ 3.50–4 35 (m, $CH_2N+ArCH_2Ar$, 10H), 7.04–7.44 (m, ArH, 8H), 7.85 (d, ArH, 4H), 8.12 (ABq, ArH, 8H); Anal. Calcd. for $C_{45}H_{36}N_8O_{14}0.5H_2O$: C, 58.63; H, 4.05. Found: C, 58.48; H, 4.22.

II. Synthesis of Chromogenic Monolabeled Tetraacid-diphenol (11)

Figure 2:
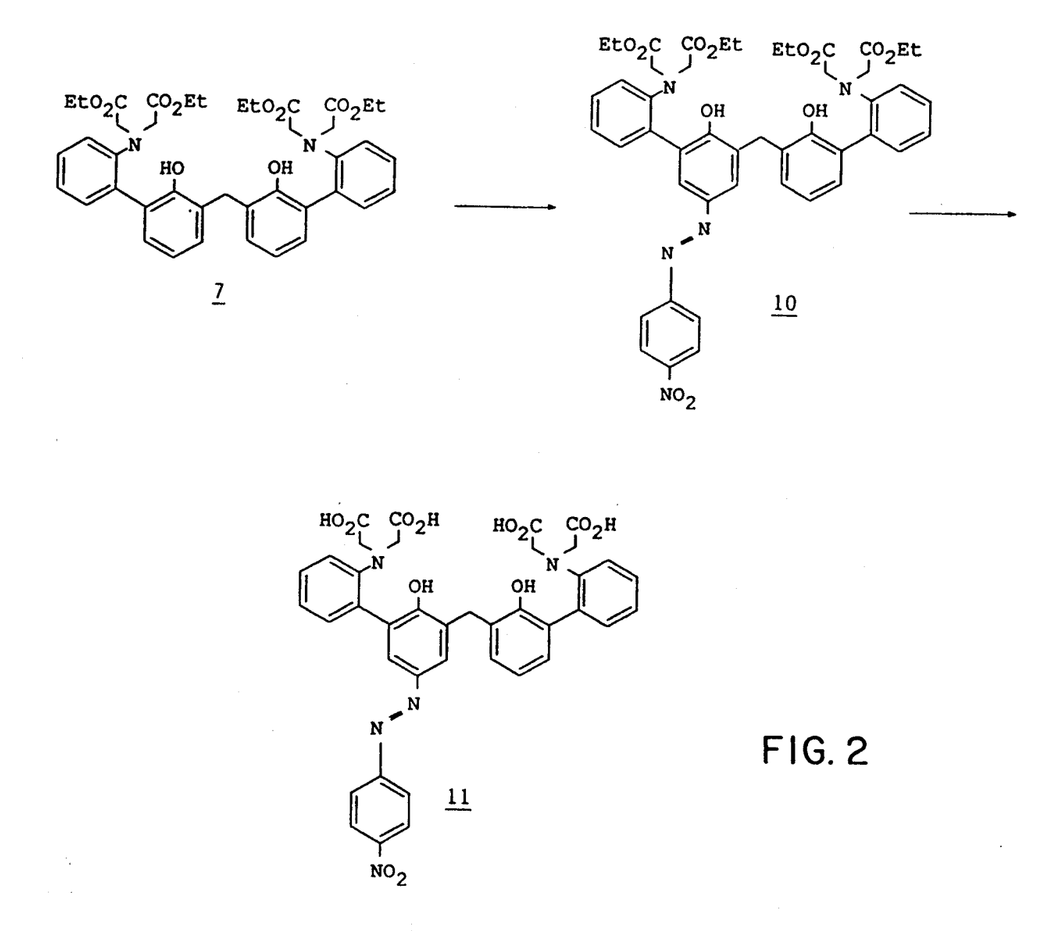
FIG. 2 describes a reaction pathway for synthesizing a chromogenic monolabeled tetraacid-diphenol of the present invention FIG. 3 describes a reaction pathway for synthesizing a chromogenic tetraacid-phenol of the present invention.

Monolabeled tetraacid-diphenol (11) was obtained from the intermediate tetraester-diphenol (7) per the synthesis described in FIG. 1 via tetraester (10) by using a 1:1 stoichiometry for the diazotization-coupling reaction followed by hydrolysis of the ester groups as shown in FIG. 2. This compound is the general formula (I) wherein R is hydrogen, X is $CH_2$; W is COH; M is p-nitrophenylazo; n is 1; and either (i) k is 1 and l is 0; or (ii) k is 0 and l is 1.

III. Synthesis of Chromogenic Tetraacid-phenol (18)

Figure 3:
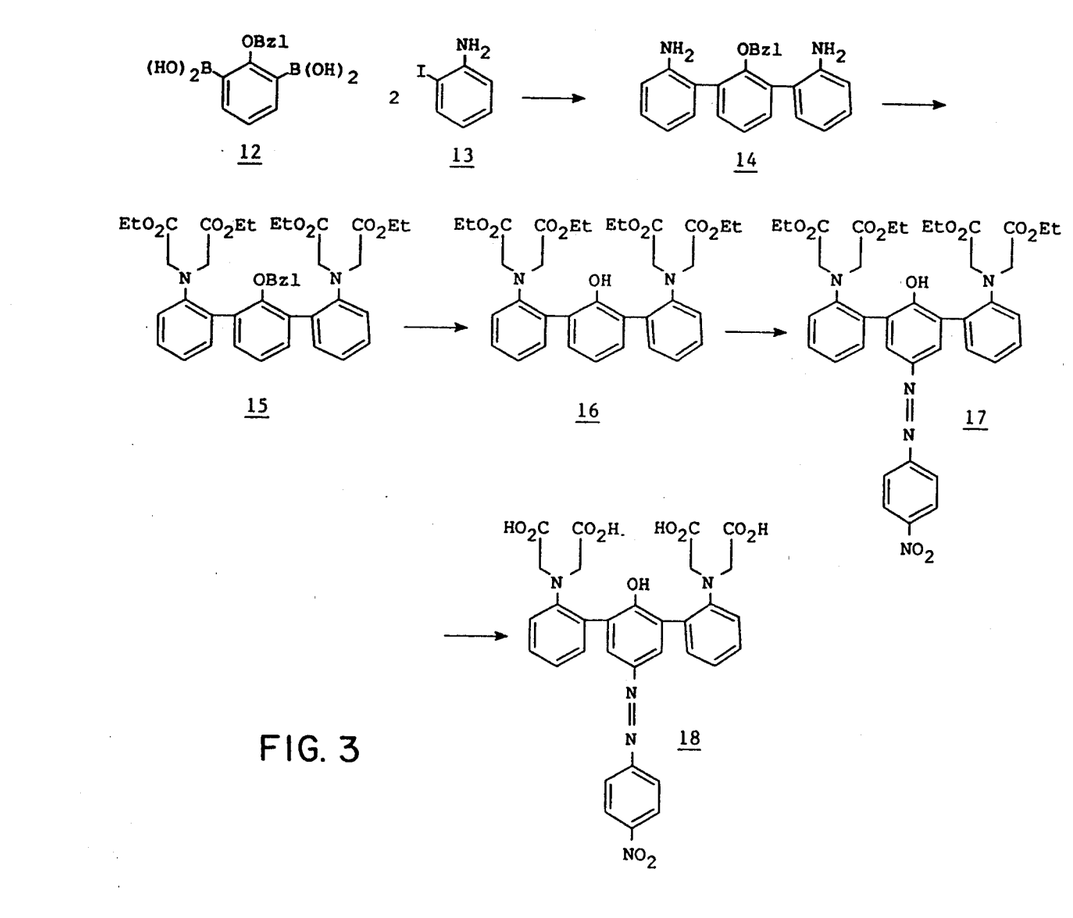

FIG. 3 illustrates the synthesis of a tri-aryl tetraacid-phenol of the present invention.

Preparation of Compound (14)

A mixture of boronic acid (12) (6.84 g, 25.1 mmol), 2-iodoaniline (13) (11.02 g, 50.3 mmol), tetrakis(triphenyl-phosphine)palladium (0.85 g, 0.74 mmol), 2M aqueous $Na_2CO_3$ (71 ml), toluene (142 ml), and ethanol (35 ml) was heated at 90° C. under argon for 48 h. An additional 90 mg of the palladium catalyst was added after 24 h. The organic layer was separated, and the aqueous layer was extracted with $CH_2Cl_2$. The combined organic extracts were dried ($MgSO_4$), the solvent was removed in vacuo. and the residue was chromatographed on silica gel with petroleum ether-EtOAc (4:1 2:1) as eluent to give diamine (14) (3.6 g, 39%) as a grey solid with mp 130°-132° C.; $^1H$ NMR($CDCl_3$): δ 3.43 (br s, $NH_2$, 4H), 4.28 (s, $CH_2O$, 2H), 6.58 (d, ArH, 2H), 6.72-6.89 (m, ArH, 4H), 7.01-7.38 (m, ArH, 10H); Anal. Calcd. for $C_{25}H_{22}N_2O\times 3.5H_2O$: C, 69.91; H, 6.81. Found: C, 69.74; H, 6.47.

Preparation of Compound (15)

A solution of diamine (14) (3.48 g, 9.50 mmol), ethyl bromoacetate (15.9 g, 95.2 mmol), and lutidine (10.2 g, 95.2 mmol) in acetonitrile (100 ml) was refluxed for 5 days. Additional amounts of ethyl bromoacetate (7.53 g, 45.1 mmol) and lutidine (5.06 g, 47.2 mmol) were added after 24 h and 48 h. The solvent was removed in vacuo, and the residue was partitioned between $CH_2Cl_2$ and water. The organic layer was dried ($MgSO_4$), the solvent was removed in vacuo, and the residue was chromatographed on silica gel with petroleum ether-EtOAc (4:1 3:1) to afford tetraester (15) (4.7 g, 69%) as white crystals with mp 120°-122° C.; $^1H$ NMR($CDCl_3$): δ 1.10 (t, $CH_3$, 12H), 3.60-4.25 (m, $CH_2O+CH_2N$, 18H), 6.51 (d, ArH, 2H), 6.95-7.62 (m, ArH, 14H); Anal. Calcd. for $C_{41}H_{46}N_2O_9$: C, 69.28; H, 6.52. Found: C, 69.34; H, 6.57.

Preparation of Compound (16)

A mixture of tetraester (15) (4.50 g, 6.33 mmol), 10% Pd/C (0.45 g), acetic acid (1 ml) and ethanol (65 ml) was shaken under hydrogen at 50 psi pressure over 24 h. Additional amount of the catalyst (200 mg) and acetic acid (2 ml) was added, and hydrogenation was continued for another 24 h. The catalyst was filtered, the solvent was removed in vacuo. and the residue was chromatographed on silica gel with petroleum ether-EtOAc (4:1) to produce (16) (3.05 g, 78%) as a pale-yellow oil; $^1H$ NMR ($CDCl_3$): δ 1.14 (t, $CH_3$, 12H), 3.94 (br s, $CH_2N$, 8H), 4.04 (q, $CH_2O$, 8H), 6.90-7.35 (m, ArH, 11H), 8.03 (br s, OH, 1H); Anal. Calcd. for $C_{34}H_{40}N_2O_9$: C, 65.79; H, 6.50. Found: C, 66.02; H, 6.48.

Preparation of Compound (18)

A mixture of tetraester-phenol (18) (2.60 g, 4.19 mmol) in THF-$H_2O$ (1:1, 50 ml) and $NaHCO_3$ (4.1 g) was cooled to 0°-5° C., and a suspension of p-nitrobenzenediazonium tetrafluoroborate (3.15 g, 13.3 mmol) in cold THF-$H_2O$ (1:1, 50 ml) was added dropwise. The mixture was stirred overnight, the solvent was removed in vacuo, and the residue was partitioned between $CH_2Cl_2$ and water. The organic layer was shaken with 2N HCl, dried ($MgSO_4$), and the solvent was removed in vacuo. The residue was chromatographed on silica gel with petroleum ether-EtOAc (3:1 1:1) to afford slightly impure tetraester (17) (~1.6 g) which was taken into the next step without further purification.

A portion of tetraester (17) (0.74 g, 0.96 mmol) was dissolved in a mixture of dioxane (32 ml) and deionized water (8 ml) containing LiOH (0.59 g, 24.5 mmol). The mixture was stirred overnight at room temperature, the solvent was removed in vacuo. and the residue was partitioned between ethyl ether and water. The aqueous layer was extracted with an additional portion of ethyl ether, and acidified with 2N HCl to pH 3.4. The aqueous layer was extracted with ethyl ether (3×30 ml), and the solvent was removed in vacuo from the combined extracts. The crude product was passed through a Dowex 50×8 acidic cation exchange column to give tetraacid (18) (0.18 g) as a dark-red glass; $^1H$ NMR ($CD_3OD$) δ 3.99 (br s, $CH_2N$, 8H), 7.0-8.5 (m, ArH, 14H); Anal. Calcd. for $C_{32}H_{27}N_5O_{11}\times 2H_2O$: C, 55.41; H, 4.50. Found: C, 55.19; H, 4.86.

This compound is that of general formula (I) in which R is hydrogen; X is $CH_2$; W is COH; M is p-nitrophenylazo; n is 0; and k is 1.

IV. Analytical Studies

1M Tetramethylammonium hydroxide (TMAOH) was purchased from Southwestern Analytical Chemicals. Triton X-100 and Brij-35 were received from ICI, and Tergitol TMN6 was purchased from Union Carbide. Analytical grade calcium chloride and magnesium chloride were used to determine the response of the calcium chromoionophores to cations. 2-(Cyclohexylamino)ethanesulfonic acid (CHES) was obtained from Calbiochem. 3,3'-thiodipropionic acid was obtained from Sigma. All materials were used as received.

A. Spectral Properties of the Calcium Chromoionophores

The UV-VIS spectra of the various forms of the calcium chromoionophores were determined in $1.0\times 10^{-4}$ M solutions of the compounds in water. A $1.0\times 10^{-2}$ M stock solution of compound was prepared in 0.05 M TMAOH. Typically the solutions were prepared as follows: 0.02 ml of the stock solution was added to 2.0 ml of the appropriate reagent. 0.1 N HCl was used to obtain the acid form (HL) and 0.1 M TMAOH for the base form (L). The resulting solutions were scanned from 700 nm to 300 nm on a Cary-3 spectrophotometer. The spectra of the cation complexes (LM+) at pH optimum were obtained by adding 0.02 ml $CaCl_2$, $MgCl_2$, both 1.0 M, to their respective cuvettes containing 2 ml of reagent and scanned from 700 nm to 300 nm.

1. Spectral Responses of Reagents Containing the Chromogenic Compounds of the Present Invention Since non-ionic surfactants are known to interact very strongly with the azophenol chromophore, their effect on the wavelength maximum of the calcium complex was examined for the various chromogenic ionophores of the present invention.

a. Chromogenic Dilabeled-tetraacid diphenol (9)

The following reagent formulation was used:

5.0×10⁻⁵ M chromogenic dilabeled tetraacid-diphenol (9) 0.1 M CHES (pH 9.0)
The spectal responses were:

| Form | λ max(ε) | λ max(ε) (1% Brij-35) |
|---|---|---|
| L | 394.0(35,160) | 407.0(35,900) |
| LCa²⁺ | 497.0(31,400) | 536.0(43,700) |
| LMg²⁺ | 427.0(27,300) | 502.0(33,300) | wherein L is the uncomplexed chromoionophore, LCa²⁺ is the calcium chromoionophore complex, and LMg²⁺ is the magnesium chromoionophore complex.

b. Chromogenic Monolabeled Tetraacid-diphenol (11)

The following reagent formulation was used:
1.0×10⁻⁴ M chromogenic monolabeled tetraaciddiphenol (11)
0.1 M CHES (pH 9.0) and the spectral responses were:

| Form | λ max(ε) | λ max(ε) (1% Brij-35) |
|---|---|---|
| L | 390.0(17,050) | 407.0(18,050) |
| LCa²⁺ | 499.0(20,630) | 512.0(20,600) |
| LMg²⁺ | 474.0(16,500) | 480.0(16,600) | c. Tetraacid-phenol (18)

The following reagent formulation was used:
1.0×10⁻⁴ M chromogenic tetraacid-phenol (18) 0.1 M CHES (pH 9.2) and the spectral responses were:

| Form | λ max(ε) | λ max(ε) (1% Brij-35) |
|---|---|---|
| L | 393.0(25,930) | 396.0(25,200) |
| LCa²⁺ | 404.0(21,080) | 469.0(19,030) |
| LMg²⁺ | 400.0(23,040) | 404.0(21,240) |

The addition of Brij-35 results in a larger bathochromic shift of the wavelength maxima upon complexation of the ionophore with calcium which effect is desirable to reduce endogenous spectral interferences.

2. Effect of Brij-35 on the Calcium Assay

Non-ionic surfactants were found to cause a substantial increase in the absorptivity of the calcium complex and attendant increase in sensitivity of the reagent. The following table shows the effect of Brij-35 on the calcium response to a reagent formulation of 1.0×10⁻⁴ M dilabeled chromogenic tetraacid diphenol (9); 0.1 M CHES; pH 9.0; 2.0 ml reagent+0.08 ml sample) for different levels of calcium.

| | ΔA500 nm | |
|---|---|---|
| Ca⁺² mg/dl | (no surfactant) | 0.1% Brij-35 |
| 0.0 | 0.0 | 0.0 |
| 4.0 | 0.134 | 0.4430 |
| 8.0 | 0.2456 | 0.7400 |
| 12.0 | 0.3466 | 0.9651 |
| 16.0 | 0.4446 | 1.1410 |

Figure 4:
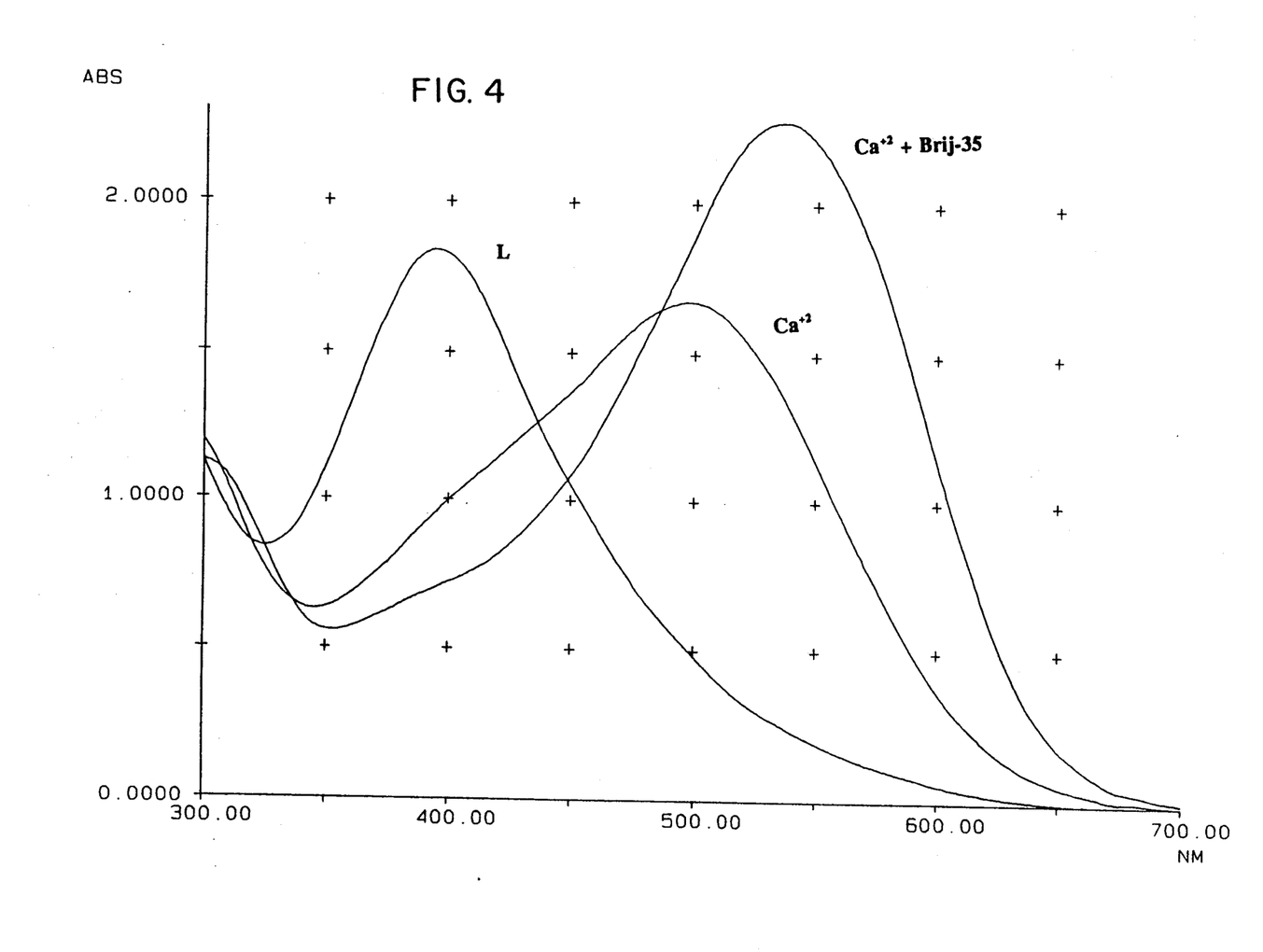
FIG. 4 illustrates the absorption response to calcium of reagent formulation including the chromogenic dilabeled tetraacid-diphenol with and without a surfactant.

These results are illustrated in FIG. 4.

3. A Preferred Reagent for Calcium Assay

A series of experiments was conducted to assess performance of the reagent containing the preferred chromogenic dilabeled tetraacid-diphenol (9) in the analysis of calcium. The following formulation was used:
2.5×10⁻⁴ M chromogenic tetraacid-diphenol (9)
0.1 M CHES (pH 9.0)
2.0 mM 8-hydroxyquinoline-5-sulfonic acid
0.1% (w/v) 3,3'-thiodipropionic acid
2.0% (w/v) Triton X-100

Samples were evaluated on a TECHNICON RA-XT® analyzer available from Miles Inc., the assignee of the present application (TECHNICON RA-XT is a registered trademark of Miles Inc., Tarrytown, N.Y.). The following instrument parameters were used:

| Reagent volume | 390 uL |
|---|---|
| Sample volume | 6 uL |
| Delay | 2 min. |
| Filter | 550 nm |
| Type | Endpoint |
| Cell pathlength | 7 mm |

Figure 5:
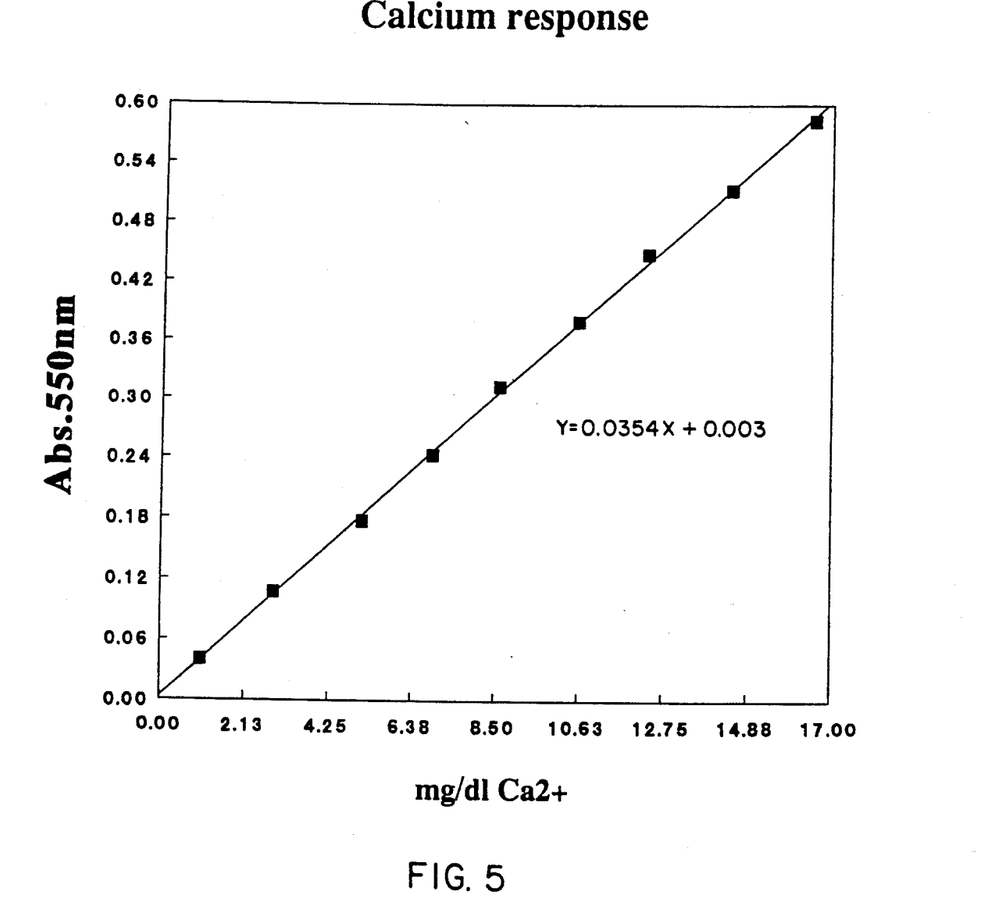
FIG. 5 illustrates the linear spectral response to calcium of a reagent composition including the chromogenic dilabeled tetraacid-diphenol.

The spectral response of the reagent composition to varying concentrations of calcium in the sample is illustrated in FIG. 5.

The sensitivity of the reagent composition was also determined, and the data is presented below:

| Ca²⁺ (mg/dl) | ΔA550 |
|---|---|
| 0.0 | 0.00 |
| 2.0 | 0.0629 |
| 4.0 | 0.1284 |
| 6.0 | 0.1917 |
| 8.0 | 0.2570 |
| 10.0 | 0.3201 |
| 12.0 | 0.3822 |
| 14.0 | 0.4409 |
| 16.0 | 0.5091 |

4. Spectral Response to Calcium of the Monolabeled Tetraacid-diphenol (11) Containing Reagent The following reagent formulation was used:
2.0×10⁻⁴ M chromogenic monolabeled tetraacid-diphenol (11)
0.1 M CHES (pH 9.0) and when 0.04 ml sample was mixed with 2.00 ml of reagent, the results were:

| Ca²⁺ (mg/dl) | ΔA500 |
|---|---|
| 0.0 | 0.000 |
| 4.0 | 0.146 |
| 8.0 | 0.2574 |
| 12.0 | 0.4136 |
| 16.0 | 0.4920 |

5. Spectral Response to Calcium of the Tetraacid-phenol (18) Containing Reagent

The following reagent formulation was used:
1.1×10⁻⁴ M chromogenic tetraacid-diphenol
0.1 M CHES (pH 9.2)
1.0% (w/v) Brij-35 and when 0.05 ml of sample was mixed with 2.00 ml of reagent, the results were:

| Ca²⁺ (mg/dl) | ΔA532 |
|---|---|
| 0.0 | 0.00 |
| 4.0 | 0.132 |
| 8.0 | 0.163 |
| 12.0 | 0.222 |

-continued

| $Ca^{2+}$ (mg/dl) | $\Delta A_{532}$ |
|---|---|
| 16.0 | 0.267 |

6. Correlation of the Method Using the Dilabeled Tetraacid-diphenol (9) Containing Reagent versus the AAS Method The reagent formulation of IV A 3 was used.

Figure 6:
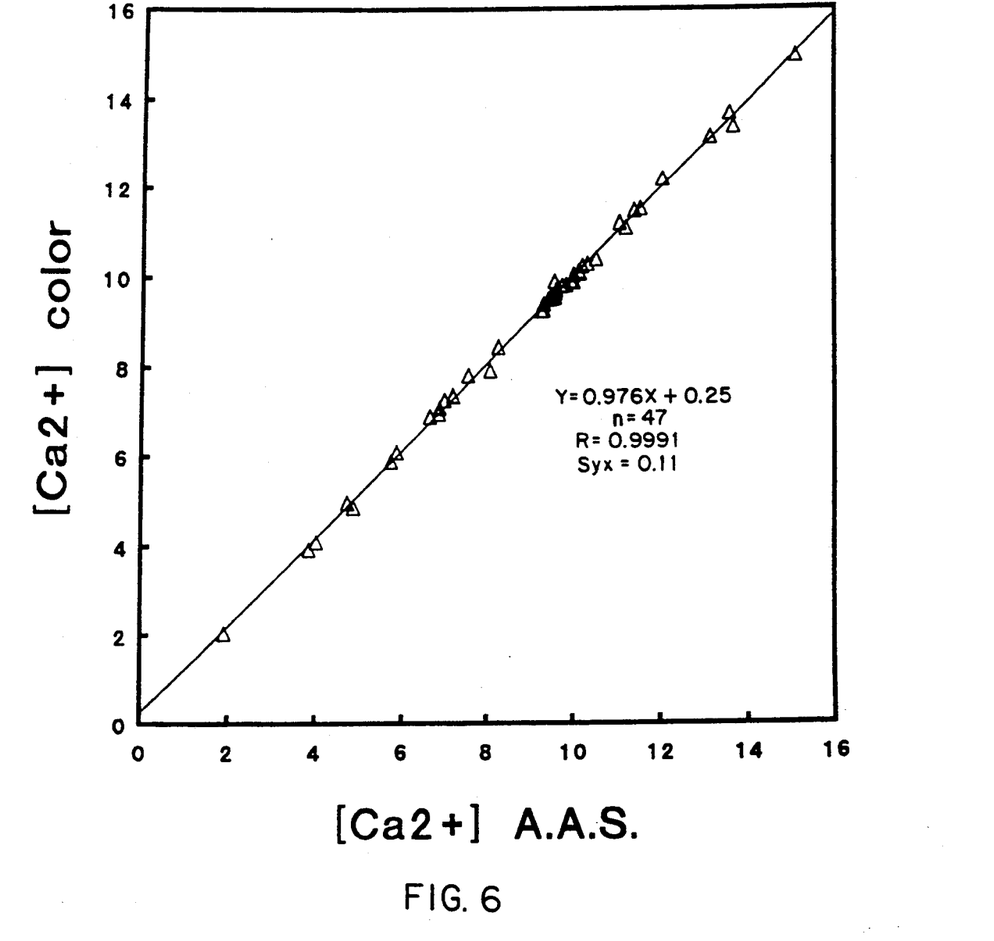
FIG. 6 is the correlation data for a reagent composition including the chromogenic dilabeled tetraacid-diphenol as compared to the atomic absorption spectrophotometric primary reference method (AAS).

Samples with less than 8 mg/dl $Ca^{+2}$ were obtained by diluting Biocell human pool serum with a diluent (aqueous 140 mM NaCl/4 mM KCl). Samples with calcium values greater than 11 mg/dl were obtained by adding aliquots of 1.0 M $CaCl_2$ to the human pool serum. The principal assay value of the RA System TM calibrator was used to calibrate the reagent during the correlation. The correlation of the new calcium method vs. the atomic absorption spectrophotometer (AAS) reference was very good (FIG. 6).

Some advantages of the present invention evident from the foregoing description include an assay method and reagent compositions utilizing chromogenic octadentate tetracarboxylic Phenols and diphenols which permit the quantitative determination of calcium in blood serum and other biological fluids by spectrophotometric methods in a homogeneous, single reagent method. The resultant assay method and reagent compositions can be easily adapted for use on an automated clinical blood analyzer.

As various changes can be made in the above compositions and method without departing from the scope of the invention, it is intended that all matter contained in the above description, or shown on the accompanying drawings, shall be interpreted as illustrative, not in a limiting sense.

What is claimed is:

1. A chromogenic compound having the structure:

where:
R is hydrogen or lower alkyl;
X is $CH_2$, $CH_2CH_2$, CH=CH, O, S, $SO_2$, S—S, or NR; and
W is CH, C—OH or N;
M is p-nitrophenylazo, 2,4-dinitrophenylazo, 2,4,6-trinitrophenylazo, p-nitrostyryl, p-benzoquinoneimino, bis-(4-dimethylaminophenyl) hydroxymethyl, 3-phenylisothiazolyl-5-azo, thiazolyl-5-azo; or isothiazolyl-5-azo;
k is 1;
l is 0 or 1; and
n is 0 or 1.

2. The chromogenic compound of claim 1 wherein R is hydrogen, X is $CH_2$, W is COH, and M is p-nitrophenylazo, and l and n are 1.

3. A composition for detecting the presence of calcium ions in solution, said composition comprising the compound of one of claims 1 or 2, a magnesium mask, a surfactant, and a buffer to adjust the pH of the reagent composition from about 8.5 to about 9.2.

4. The composition of claim 3 wherein the surfactant is Present at a concentration of about 2% weight to volume.

5. The composition of claim 3 wherein the surfactant is a polyethyleneoxide alkyl ether.

6. The composition of claim 3 further including an antioxidant.

7. A method for selectively determining the presence of calcium ions in a test sample comprising the steps of:
(a) contacting said test sample with a reagent composition including a compound which complexes selectively to the test cation and being the formula:

where:
R is hydrogen or lower alkyl;
X is $CH_2$, $CH_2CH_2$, CH=CH, O, S, $SO_2$, S—S or NR; and
W is CH, C—OH or N; and
M is p-nitrophenylazo, 2,4-dinitrophenylazo, 2,4,6-trinitrophenylazo, p-nitrostyryl, p-benzoquinoneimino, bis-(4-dimethylaminophenyl) hydroxymethyl, 3-phenylisothiazolyl-5-azo, thiazolyl-5-azo; or isothiazolyl-5-azo;
k is 1;
l is 0 or 1; and
n is 0 or 1;
(b) measuring the detectable response; and
(c) comparing the response so detected with responses measured when said compound is reacted with a series of standard compositions containing known amounts of calcium ions.

8. The method of claim 7 wherein R is hydrogen, X is $CH_2$, W is COH, and M is p-nitrophenylazo, and l and n are 1.

9. The method of claim 7 wherein said reagent composition further includes a magnesium mask, a surfactant and a buffer to maintain the pH of the reagent composition at from about 8.5 to about 9.2.

10. The method of claim 9 wherein the surfactant is present at a concentration of about 2% weight to volume.

11. The method of claim 9 wherein the surfactant is a polyethyleneoxide alkyl ether.

12. The method of claim 7 wherein the reagent composition further includes an antioxidant.

* * * * *